United States Patent

Hyodo et al.

(10) Patent No.: US 9,304,110 B2
(45) Date of Patent: Apr. 5, 2016

(54) CARBURIZATION SENSING METHOD

(75) Inventors: Shigetoshi Hyodo, Tokyo (JP); Yoshikazu Takimoto, Tokyo (JP)

(73) Assignee: NIPPON STEEL & SUMITOMO METAL CORPORATION, Tokyo (JP)

(*) Notice: Subject to any disclaimer, the term of this patent is extended or adjusted under 35 U.S.C. 154(b) by 174 days.

(21) Appl. No.: 14/349,722

(22) PCT Filed: Aug. 8, 2012

(86) PCT No.: PCT/JP2012/070159
§ 371 (c)(1),
(2), (4) Date: Apr. 4, 2014

(87) PCT Pub. No.: WO2013/061667
PCT Pub. Date: May 2, 2013

(65) Prior Publication Data
US 2014/0239944 A1    Aug. 28, 2014

(30) Foreign Application Priority Data
Oct. 25, 2011  (JP) .................................. 2011-233881

(51) Int. Cl.
*G01N 27/82* (2006.01)
*C23C 8/20* (2006.01)
*C23C 8/22* (2006.01)

(52) U.S. Cl.
CPC ....... *G01N 27/82* (2013.01); *C23C 8/20* (2013.01); *C23C 8/22* (2013.01)

(58) Field of Classification Search
CPC .. G01N 27/82; G01N 27/902; G01N 27/9033
USPC ............................ 324/240, 239, 217, 219, 260
See application file for complete search history.

(56) References Cited

U.S. PATENT DOCUMENTS

| | | | | |
|---|---|---|---|---|
| 5,270,647 A | * | 12/1993 | Beissner et al. | 324/240 |
| 2003/0169035 A1 | * | 9/2003 | Crouzen | 324/230 |

FOREIGN PATENT DOCUMENTS

| | | |
|---|---|---|
| JP | 62-853 | 1/1987 |
| JP | 62-6153 | 1/1987 |
| JP | 3-253555 | 11/1991 |
| JP | 4-145358 | 5/1992 |
| JP | 05-052815 | 3/1993 |
| JP | 6-88807 | 3/1994 |
| JP | 11-223539 | 8/1999 |
| JP | 2000-266727 | 9/2000 |
| JP | 2004-279054 | 10/2004 |
| JP | 2004-279055 | 10/2004 |
| JP | 2007-040865 | 2/2007 |
| JP | 2010-197222 | 9/2010 |

* cited by examiner

*Primary Examiner* — Tung X Nguyen
*Assistant Examiner* — Dominic Hawkins
(74) *Attorney, Agent, or Firm* — Clark & Brody

(57) ABSTRACT

The present invention provides a method for sensing whether carburization occurs or not on an inner surface of a pipe or tube by an electromagnetic testing, comprising: a first step of inserting a carburized tube P0 into an excitation coil 11 and into a detection coil 12, and determining a value of a parameter K; and a second step of setting conditions of the excitation coil so as to obtain the value of the parameter K determined in the first step, and thereafter, inserting a pipe or tube that is an inspection target into the excitation coil 11 and into the detection coil 12 and sensing whether carburization occurs or not on an inner surface of the pipe or tube based on an output signal outputted from the detection coil 12.

2 Claims, 4 Drawing Sheets

CARBURIZATION SENSING METHOD

TECHNICAL FIELD

The present invention relates to a method for sensing whether carburization occurs or not on an inner surface of a pipe or tube by an electromagnetic testing such as an electromagnetic induction testing and a magnetic flux leakage testing. Hereinafter, "pipe or tube" is referred to as "tube" when deemed appropriate.

BACKGROUND ART

It is known that among various steel materials, austenitic stainless steel is susceptible to carburization. For example, a cracking tube, which is used for the thermal decomposition reaction in an ethylene manufacturing process of a petrochemical plant, is made of austenitic stainless steel, and carburization occurs on its inner surface after being used for long hours. Moreover, in the manufacturing process of the cracking tube, carburization occurs when heat treatment is performed in a poorly degreased condition of lubricant. Since the occurrence of such carburization may cause significant reduction of the life of the cracking tube, there is a need for accurately sensing whether carburization occurs or not.

For this reason, conventionally, an electromagnetic test such as an electromagnetic induction test is carried out on a cracking tube installed in a plant as a nondestructive inspection across the entire length of the cracking tube at the time of periodic maintenance of the plant so that whether carburization occurs or not is sensed based on the magnitude of the output value thereof. Moreover, also in the manufacturing process of a cracking tube, whether carburization occurs or not is sensed by performing an electromagnetic test across its entire length or by cutting off both ends thereof and performing a microstructure observation thereon.

In general, if a seamless tube is subjected to drawing-working in a producing process, the tube has smaller roughness in the inner surface, so that amount of lubricant adhering on the inner surface becomes smaller. Hence, heat treatment in a poorly degreased condition causes microscopic carburization. Particularly, if the drawing-working is performed in a high-pressure container, the inner surface of the tube becomes almost equal to a mirror surface, and thus carburization due to the poor degrease becomes extremely microscopic.

There have been suggested various methods of sensing whether carburization occurs or not including those that have not been put to practical use (see Patent Literature 1 to Patent Literature 7, for example), but none of these methods can sense the aforementioned microscopic carburization.

CITATION LIST

Patent Literature

[Patent Literature 1] JP3-253555A
[Patent Literature 2] JP62-6153A
[Patent Literature 3] JP4-145358A
[Patent Literature 4] JP6-88807A
[Patent Literature 5] JP2000-266727A
[Patent Literature 6] JP2004-279054A
[Patent Literature 7] JP2004-279055A

SUMMARY OF INVENTION

Technical Problem

An object of the present invention, which has been made in order to solve the problems according to the conventional art, is to provide a carburization sensing method capable of sensing even microscopic carburization that is difficult to be sensed by conventional carburization sensing methods.

Solution to Problem

In order to solve the above problems, as described in JP 2010-197222A suggested by the present inventors, a ferrite meter was oppositely disposed to an outer surface of a tube having microscopic carburization on an inner surface thereof so as to measure magnetic strength (amount of ferrite) at its carburized portion with this ferrite meter, but no effective indicated values could be obtained. Specifically, the magnetic strength was measured at ten positions of the tube where it was confirmed through a microstructure observation that microscopic carburization had occurred on the inner surface thereof, but all the indicated values of the ferrite meter were 0.01 Fe % or less. It may be estimated that such small magnetic strength results from small amount of production of an oxide magnetic material caused by the carburization.

Based on the above described result, first, the present inventors attempted to sense microscopic carburization not from the outer surface of the tube, but from the inner surface thereof. Specifically, using a common inner coil for flaw inspection, a test of confirming whether it is possible or not to sense carburization was performed under the following conditions (1) to (3). For the evaluation, a detection signal (absolute value signal) outputted from the inner coil was amplified, and thereafter was subjected to synchronous detection, thereby separating and extracting a first signal component and a second signal component each of which had a different phase by 90° from each other. Each phase of the first signal component and the second signal component was rotated (shifted) by the same predetermined amount, and the first signal component after the rotation was defined as an X signal, and the second signal component after the rotation was defined as a Y signal. The amount of the above rotation (amount of phase shift) was determined such that, if the X signal and the Y signal are expressed on the X-Y vector plane, the Y axis direction on the X-Y vector plane corresponds to variation in liftoff of the tube, and the X axis direction corresponds to variation in magnetic property of the tube.

(1) Inspection target: 13 steel tubes each having microscopic carburization on its inner surface, and having an outer diameter of 19 mm, and an inner diameter of 17 mm
(2) Inner coil: outer diameter of 16.5 mm, length of 2 mm, impedance of 50 Ω/100 kHz
(3) Excitation frequency (inspection frequency): 25 kHz Using steel tubes of the same type as that of the above inspection targets, and having no carburization, a magnetic tape was wound around the inner surface of each tube by 2.5 turns and 6 turns, respectively, and detection signals obtained from these magnetic tapes were evaluated in the same manner.

FIG. 1 is a diagram showing results of the above test (diagram showing the X signals and the Y signals on the X-Y vector plane). In FIG. 1, data plotted with white rectangles indicate data obtained from the carburized portion of each inspection target, and data plotted with black rectangles indicate data obtained from the magnetic tapes.

The flaw inspection using the inner coil as described in the above test senses change in electric resistance due to flaws, and this inspection is usually carried out with high sensitivity, so that this inspection is sensitive to variation in magnetic property. In the case of having variation in magnetic property, the X signal becomes a negative value depending on the magnitude of the variation in magnetic property (data is plotted in the negative direction of the X axis). However, except for the data indicated by the arrows A, B, and C in FIG. 1, the data obtained from the carburized portions of the inspection targets became positive values, and no carburization could be sensed. Although the data indicated by the arrows A, B, and C in FIG. 1 were negative values, even data indicating the negative value which has the greatest absolute value (data indicated by the arrow A) had approximately the same signal strength of the X signal as that of the X signal of the data obtained from the magnetic tape whose number of windings was 6 turns, which exhibited extremely weak variation in magnetic property.

It is difficult to sense microscopic carburization using a common inner coil for flaw inspection because excitation ability (magnetic field strength) to be used is weak. To be specific, the magnetization characteristics of a magnetic material are expressed by a B-H curve, and initial permeability is extremely small if the magnetic field strength is small, and the magnetic permeability increases as the magnetic field strength increases. Hence, it has been found that it is impossible for a common inner coil used for flaw inspection to sense microscopic carburization that causes only weak variation in magnetic property.

For sensing microscopic variation in magnetic property, it is preferable to employ a mutual induction method that separately provides an excitation coil and a detection coil, but in the case of using an inner coil, it is difficult to employ the mutual induction method using an excitation coil in a large size for the reason of limitation of the dimension of a coil to be inserted in a tube. In order to increase the magnetic field strength, it is required to supply a greater excitation current by increasing a winding diameter of the excitation coil and a diameter of an electric cable having a length of dozens of meters for supplying the excitation current to the excitation coil, but the inner diameter of the tube is limited. Even if the diameter of the electric cable is increased so as to increase the excitation current, generated heat of the excitation coil also increases, which causes variation in temperature in the detection coil, and this may make it difficult to obtain a stable detection signal (absolute value signal).

In addition, the inner coil is supposed to be moved inside the tube, but it is difficult to move the inner coil at a high speed thereinside, and it is also required to retrieve the inner coil inserted in the tube, which is not suitable for automatic inspection in the production line of the tube.

Based on the results of the above test, the present inventors have re-studied on a method of sensing whether carburization occurs or not on the inner surface of the tube that is the inspection target from the outer surface of the tube. Specifically, first the present inventors have studied on whether it is possible to detect the magnetic tape attached onto the inner surface of each tube under the following conditions, using the method shown in FIG. 1 of JP2010-197222A suggested by the present inventors (referred to as a "conventional method", hereinafter). Variation in magnetic property caused by microscopic carburization to be actually sensed is weak; therefore various tapes having various numbers of windings: 1 turn, 3 turns, and 5 turns were used. The magnetic strength (amount of ferrite) of each magnetic tape attached on the inner surface of each tube was measured with a ferrite meter.
(1) Excitation frequency (inspection frequency): 500 Hz
(2) Excitation current: 0.01 A
(3) Number of windings of excitation coil: 200 turns
(4) Length of excitation coil: 70 mm The results of the above test are shown in Table 1.

TABLE 1

| Number of Turns | Magnetic Strength (Fe %) | X Axis Signal (mV) |
| --- | --- | --- |
| 5 | 0.035 | −50 |
| 3 | 0.035 | Undetectable |
| 1 | 0.01 or less | Undetectable |

As shown in Table 1, in the conventional method, it was impossible to detect the magnetic tapes of which number of windings is 3 turns or less. In other words, weak variation in magnetic property could not be sensed under the aforementioned conditions; therefore it may be considered that microscopic carburization cannot be sensed.

In the method of sensing whether carburization occurs or not on the inner surface of the tube from the outer surface of the tube, the present inventors have further conducted enthusiastic studies on influence of the excitation ability (magnetic field strength) and the excitation frequency on the sensing performance of the microscopic carburization (weak variation in magnetic property) as follows.

(1) Influence of Excitation Ability (Magnetic Field Strength)

In the case of employing the mutual induction method that separately provides the excitation coil and the detection coil, as the magnetic field strength (product of the excitation current and the number of windings of the excitation coil per unit length) increases, the voltage induced in the detection coil increases. Hence, it is possible to reduce sensitivity of the signal processing section for processing an output signal from the detection coil (gain of the amplifier included in the signal processing section), thereby attaining such an advantage that reduces electric noises. As aforementioned, however, the magnetization characteristics of a magnetic material are expressed by the B-H curve, and initial permeability is extremely small if the magnetic field strength is small, and the magnetic permeability increases until the maximum value is reached in accordance with increase of the magnetic field strength. If the magnetic field is further increased, the magnetic flux density becomes saturated, and the magnetic permeability rather becomes smaller. Hence it is difficult to sense weak variation in magnetic property unless an appropriate magnetic field strength is provided. In other words, if the magnetic permeability is small, variation of the output signal (output voltage) of the detection coil due to the variation in magnetic property is so small that weak variation in magnetic property cannot be sensed. In this case, if the sensitivity of the signal processing section is increased for correction, electric noises increase, which hinders appropriate inspection.

Accordingly, the sensing performance of microscopic carburization (weak variation in magnetic property) depends on the excitation ability (magnetic field strength) in the light of maximizing the magnetic permeability.

(2) Influence of Excitation Frequency

In the case of sensing variation in magnetic property caused by carburization on the inner surface of the tube from the outer surface of the tube, it is required to set the excitation frequency to be a low frequency in order to reduce the influence of the skin effect, and increase the penetration depth. Meanwhile, in the case of employing the mutual induction method, if the excitation frequency is set to be an excessively low frequency, the voltage induced in the detection coil becomes small, and thus it is required to increase the sensitivity of the signal processing section for processing the output signal of the detection coil (gain of the amplifier included in the signal processing section). Consequently, electric noises are increased, which may hinder appropriate inspection.

Accordingly, the sensing performance of microscopic carburization depends on the excitation frequency. To be specific, it may be considered that the penetration depth roughly has a positive correlation with the excitation frequency to the power of −½, and the sensitivity of the signal processing section (electric noise) has a negative correlation with the excitation frequency (in other words, this has a positive correlation with the excitation frequency to the power of −1); therefore, it was found that the sensing performance of microscopic carburization depends on the excitation frequency to the power of −3/2.

The present inventors considered that, based on the results of the above studies, a parameter K represented by the following Equation (1) can be an index of the carburization sensing performance, where the current value of an excitation current passing through the excitation coil is defined as I(A), the length of the excitation coil is defined as L (mm), the number of windings of the excitation coil is defined as N, and the frequency of the excitation current passing through the excitation coil is defined as F (kHz).

$$K=(I \cdot N/L) \cdot F^{-3/2} \tag{1}$$

FIG. 2 is a diagram showing an example of test results from investigation on a relation between detection signals obtained from magnetic tapes attached on inner surfaces of tubes having no carburization and a parameter K using a mutual induction method. In FIG. 2, the abscissa indicates the parameter K, and the ordinate indicates the detection signal. To be specific, in this test, the value of the parameter K was varied by using various conditions (excitation current, etc.) of the excitation coil 11 using an eddy current testing apparatus 100 described in FIG. 3, which is described below. The values of the detection signals (to be specific, the X axis signal obtained by processing the absolute value signal outputted from the detection coil 12) obtained from the magnetic tapes whose number of windings were 1 turn and 3 turns were evaluated.

As shown in FIG. 2, as the value of the parameter K is increased, the absolute value of the detection signal (X axis signal) obtained from each magnetic tape increases (that is, the carburization sensing performance is enhanced), which exhibits a relatively preferable correlation therebetween. From the above results, the present inventors have confirmed that the parameter K can be an index of the carburization sensing performance. The present inventors have also found that it is possible to sense microscopic carburization by appropriately adjusting the value of the parameter K.

The present invention has been accomplished based on the above findings of the present inventors.

Specifically, the present invention includes the following first and second steps.

(1) First Step

A first step is a step of inserting a carburized pipe or tube in which occurrence of carburization on an inner surface thereof is known into an excitation coil and into a detection coil, and determining a value of a parameter K represented by the following Equation (1):

$$K=(I \cdot N/L) \cdot F^{-3/2} \tag{1}$$

so as to sense the carburization that has occurred in the carburized pipe or tube based on an output signal outputted from the detection coil, where a current value of an excitation current passing through the excitation coil is defined as I(A), a length of the excitation coil is defined as L (mm), a number of windings of the excitation coil is defined as N, and a frequency of the excitation current passing through the excitation coil is defined as F (kHz).

(2) Second Step

A second step is a step of setting conditions of the excitation coil so as to obtain the value of the parameter K determined in the first step, and thereafter, inserting a pipe or tube that is an inspection target into the excitation coil and into the detection coil and sensing whether carburization occurs or not on an inner surface of the pipe or tube based on an output signal outputted from the detection coil.

According to the present invention, in the first step, it is configured to determine the value of the parameter K so as to sense carburization of the carburized pipe or tube. As apparent from Equation (1), this parameter K is proportional to the magnetic field strength (I·N/L), and also proportional to the excitation frequency F to the power of −3/2. As described above, the carburization sensing performance depends on the magnetic field strength and the excitation frequency to the power of −3/2, and thus it may be considered that the parameter K represented by Equation (1) is an index indicating the carburization sensing performance. Accordingly, in order to sense microscopic carburization, it is only required to prepare a pipe or tube having microscopic carburization as the carburized pipe or tube, and determine the value of the parameter K, that is, adjust the carburization sensing performance so as to sense this carburization.

According to the present invention, in the second step, after the conditions of the excitation coil are so set as to obtain the value of the parameter K determined in the first step, it is configured to sense whether the carburization occurs or not on the inner surface of the pipe or tube that is the inspection target. As aforementioned, since the value of the parameter K is so determined as to sense the carburization of the carburized pipe or tube in the first step, it may be expected that only by inspecting a pipe or tube that is an inspection target after the conditions of the excitation coil are adjusted such that the determined value of the parameter K is obtained, the carburization in this pipe or tube, which is substantially equal to the carburization in the carburized pipe or tube used for determining the value of the parameter K, can also be sensed.

The present inventors have conducted studies on sensing microscopic carburization, and to be specific, they have found that it is preferable to set the value of the parameter K to satisfy 4≤K≤8.

That is, in the second step, the conditions of the excitation coil are set such that the value of the parameter K satisfies 4≤K≤8.

Advantageous Effect of Invention

According to the carburization sensing method of the present invention, it is possible to sense microscopic carburization that is difficult to be sensed by conventional carburization sensing methods.

DESCRIPTION OF EMBODIMENT

Hereafter, with reference to the appended drawings, an embodiment of the present invention will be described taking an example of a case in which a tube is a steel tube, and an eddy current test is performed as the electromagnetic test.

Figure 1:
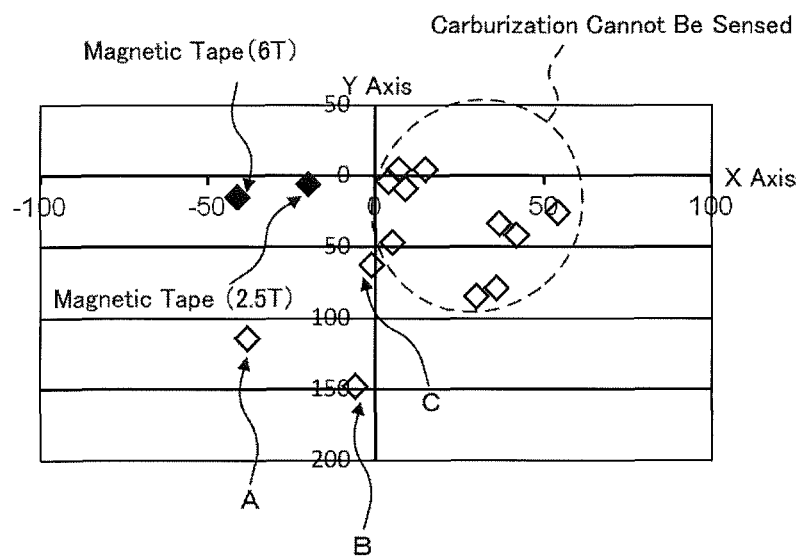
FIG. 1 is a diagram showing results of a test carried out using an inner coil by the present inventors.
Figure 2:
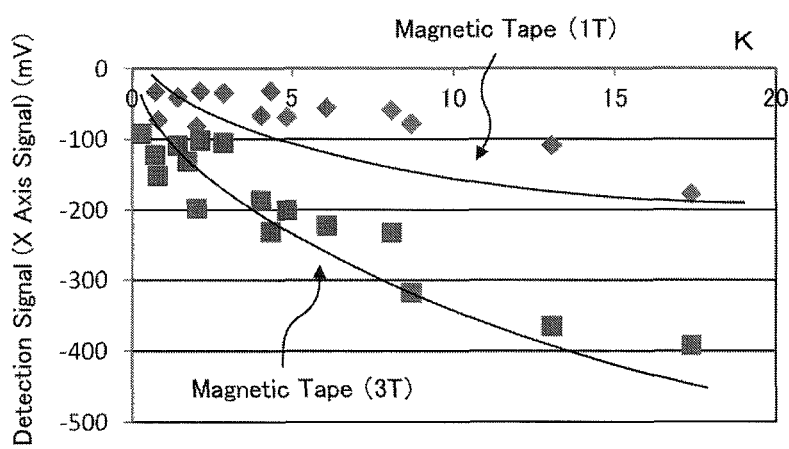
FIG. 2 is a diagram showing an example of test results from investigation on a relation between detection signals obtained from magnetic tapes attached on inner surfaces of tubes having no carburization and a parameter K using a mutual induction method.
Figure 3:
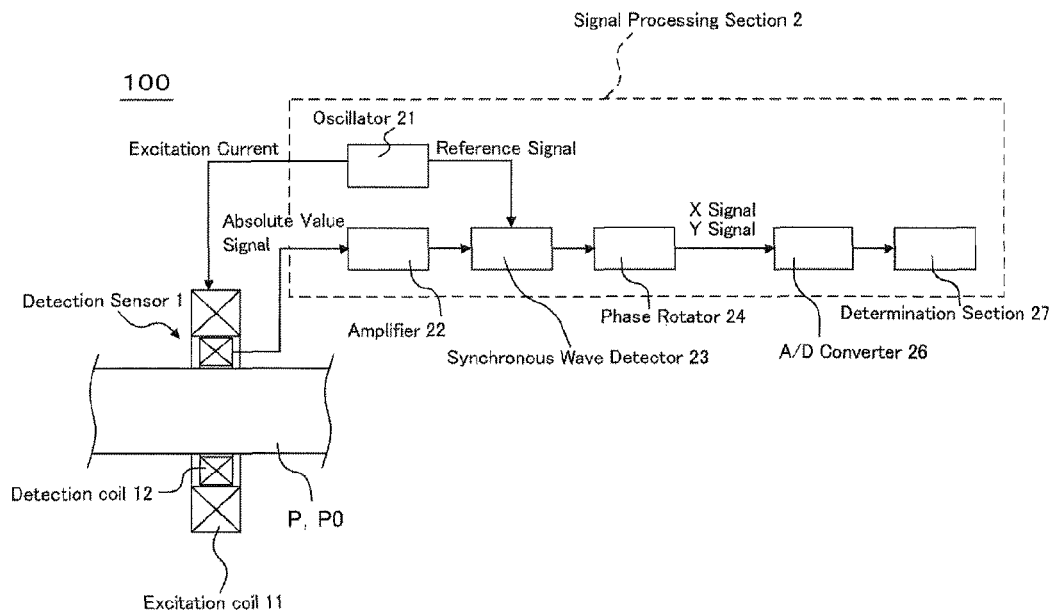
FIG. 3 is a schematic diagram showing an outline configuration of an eddy current testing apparatus used for a carburization sensing method according to an embodiment of the present invention.

FIG. 3 is a schematic diagram showing an outline configuration of an eddy current testing apparatus used for a carburization sensing method according to an embodiment of the present invention.

As shown in FIG. 3, an eddy current testing apparatus 100 of the present embodiment includes a detection sensor 1 and a signal processing section 2. In FIG. 3, the detection sensor 1 is shown in a cross sectional view.

The detection sensor 1 is configured to apply an alternating magnetic field to a steel tube P thereby inducing an eddy current, and detect the eddy current induced in the steel tube P. To be specific, the detection sensor 1 of the present embodiment includes an excitation coil 11 that applies an alternating magnetic field to the inserted steel tube P, and a detection coil 12 that detects the eddy current induced in the inserted steel tube P.

The signal processing section 2 is configured to pass an alternating excitation current through the detection sensor 1 and sense whether carburization occurs or not on the inner surface of the steel tube P based on a detection signal (absolute value signal) outputted from the detection sensor 1. To be specific, the signal processing section 2 of the present embodiment includes an oscillator 21, an amplifier 22, a synchronous wave detector 23, a phase rotator 24, an A/D converter 26, and a determination section 27.

The oscillator 21 supplies an alternating excitation current to the detection sensor 1 (to be specific, the excitation coil 11 of the detection sensor 1). This causes an alternating magnetic field to be applied to the steel tube P, and the eddy current is induced in the steel tube P as described above.

An absolute value signal outputted from the detection sensor 1 (to be specific, the detection coil 12 of the detection sensor 1) is amplified by the amplifier 22, and thereafter outputted to the synchronous wave detector 23.

The synchronous wave detector 23 performs synchronous wave detection of the output signal of the amplifier 22 based on the reference signal outputted from the oscillator 21. To be specific, a first reference signal having the same frequency and the same phase as those of the excitation current to be supplied to the detection sensor 1, and a second reference signal of which phase is shifted by 90° from the phase of the first reference signal are outputted from the oscillator 21 to the synchronous wave detector 23. Then, the synchronous wave detector 23 separates and extracts a signal component (first signal component) that is in phase with the phase of the first reference signal and a signal component (second signal component) that is in phase with the phase of the second reference signal from the output signal of the amplifier 22. The separated and extracted first and second signal components are outputted to the phase rotator 24, respectively.

The phase rotator 24 rotates (shifts) the phases of the first signal component and the second signal component outputted from the synchronous wave detector 23 by the same predetermined amount, and outputs the first signal component as an X signal and the second signal component as a Y signal to the A/D converter 26, for example. It is noted that the X signal and the Y signal that are outputted from the phase rotator 24 correspond to components of a signal waveform projected to the X axis and the Y axis, respectively in an X-Y vector plane represented by two mutually orthogonal axes (X axis and Y axis), where the signal waveform is so-called a Lissajous figure and used for flaw inspection (that is, an absolute value signal waveform (to be precise, an absolute value signal waveform after being amplified by the amplifier 22) of the detection sensor 1 represented by a polar coordinate (Z, θ) where Z is amplitude and θ is phase).

Figure 4:
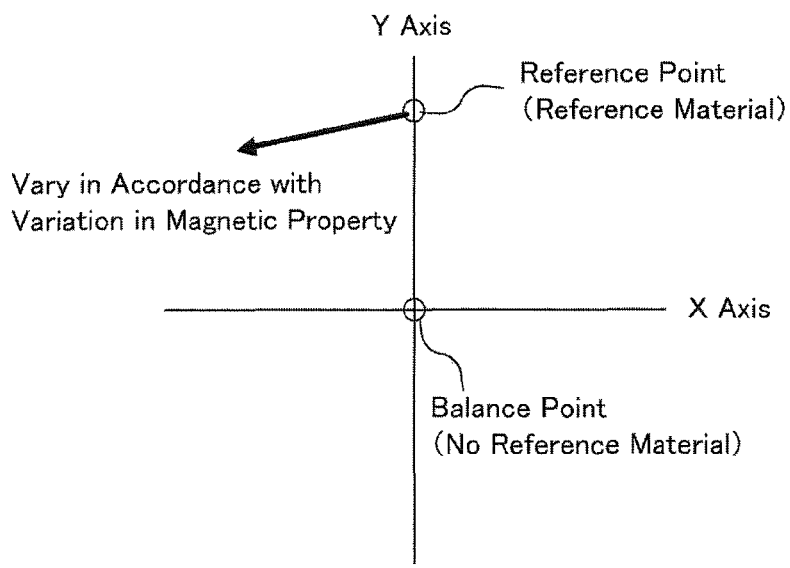
FIG. 4 is a schematic diagram representing on an X-Y vector plane an X signal and Y signal outputted from a phase rotator included in the eddy current testing apparatus shown in FIG. 3.

FIG. 4 is a schematic diagram representing on an X-Y vector plane an X signal and Y signal outputted from a phase rotator 24.

In a state in which a steel tube having no carburization on its inner surface (referred to as a "reference material", hereinafter) is not inserted into the detection sensor 1, the balancing quantity of a balance circuit (not shown) which is disposed in the preceding stage of the amplifier 22 is adjusted such that the X signal and the Y signal become zero (such that a spot corresponding to the front edge of a vector of which X axis component and Y axis component are the X signal and the Y signal, respectively is located at a balance point (an origin point) shown in FIG. 4) so that the first signal component and the second signal component, which are outputted from the synchronous wave detector 23, are zero, respectively.

Next, the reference material is inserted into the detection sensor 1 and halted thereat, and the amplification factor of the amplifier 22 and the phase rotation amount of the phase rotator 24 are adjusted such that the X signal equals zero and the Y signal equals a predetermined voltage (for example, 4V) (such that the front edge of a vector is located at the reference point shown in FIG. 4).

After the above described adjustment is performed in advance, the steel tube P that is an inspection target is moved in the axial direction, and inserted into the detection sensor 1, thereby acquiring the X signal and the Y signal.

The A/D converter 26 performs A/D conversion of the output signal of the phase rotator 24, and outputs it to the determination section 27.

The determination section 27 senses whether carburization occurs or not on the inner surface of the steel tube P based on the output data of the A/D converter 26 (that is, digital data obtained through A/D conversion of X signal and Y signal. Hereafter, referred to as X signal data and Y signal data). As shown in FIG. 4, the position of the front edge of the vector varies in accordance with variation in magnetic property of the steel tube P, and this variation becomes greater in the X axis direction than in the Y axis direction. Hence, the determination section 27 of the present embodiment senses whether carburization occurs or not using the X signal data of the X signal data and the Y signal data that have been inputted. To be specific, the determination section 27 of the present embodiment compares the inputted X signal data with a threshold value which is determined and stored in advance, and determines that carburization has occurred on the inner surface of the steel tube P if the X signal data exceeds the threshold value, and determines that carburization has not occurred on the inner surface of the steel tube P if the X signal data is within the aforementioned threshold value.

In order to sense the carburization on the inner surface of the steel tube P using the eddy current testing apparatus 100 having the above described configuration, a carburized tube P0 in which occurrence of microscopic carburization on an inner surface thereof is known is inserted into the excitation coil 11 and the detection coil 12 in advance (see FIG. 3). A value of the parameter K represented by the following Equation (1) is so determined as to sense the carburization that has occurred in the carburized tube P0 based on the output signal (to be specific, X signal data) outputted from the detection coil 12.

$$K=(I \cdot N/L) \cdot F^{-3/2} \qquad (1)$$

In the above Equation (1), I represents a current value (A) of the excitation current passing through the excitation coil 11, L represents a length (mm) of the excitation coil 11, N represents the number of windings of the excitation coil 11, and F represents a frequency (kHz) of the excitation current passing through the excitation coil 11.

After the conditions of the excitation coil 11 (the current value of the excitation current, the length of the excitation coil, the number of windings of the excitation coils, and the frequency of the excitation current) are so set as to obtain the value of the parameter K determined in the above manner, the steel tube P that is the inspection target is inserted into the excitation coil 11 and the detection coil 12 so as to sense whether carburization occurs or not on the inner surface of the steel tube P based on the output signal (to be specific, X signal data) from the detection coil 12.

Figure 5:
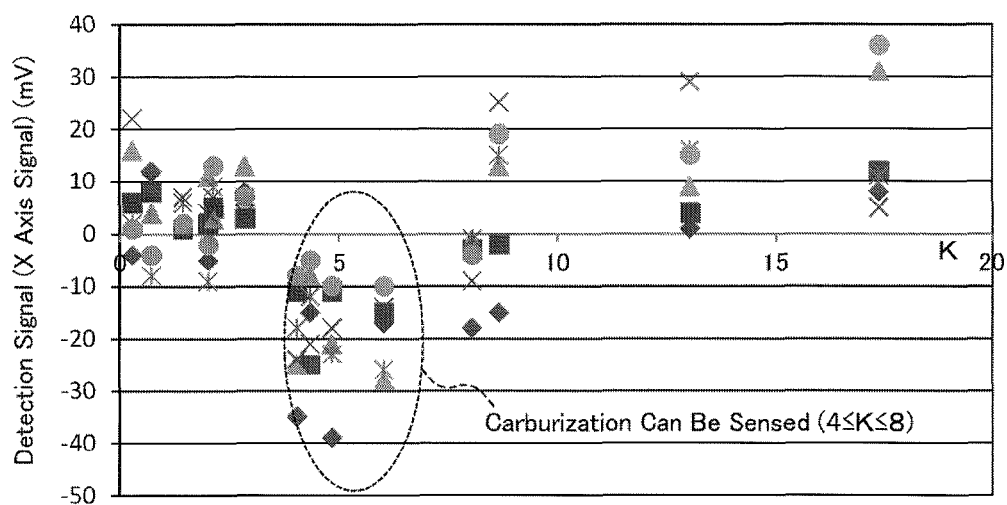
FIG. 5 is a diagram showing an example of test results from investigation regarding a relation between detection signals obtained from plural carburized tubes using the eddy current testing apparatus shown in FIG. 3, and the parameter K.

FIG. 5 is a diagram showing an example of test results from investigation regarding a relation between detection signals obtained from plural carburized tubes P0 using the eddy current testing apparatus 100, and the parameter K under the following conditions. In FIG. 5, the abscissa represents the parameter K, and the ordinate represents the detection signals. To be specific, in this test, it was configured to vary the value of the parameter K by using various conditions of the excitation coil 11 of the eddy current testing apparatus 100. The values of the detection signals (to be specific, X axis signal obtained by signal-processing absolute value signals outputted from the detection coil 12) obtained from the plural carburized tubes P0 were evaluated. In FIG. 5, data plotted with the identical symbol were obtained from the identical carburized tube P0. The carburized portion of each carburized tube P0 had a magnetic strength (amount of ferrite) of 0.01 Fe % or less.

<Test Conditions>
(1) Frequency of excitation current F: 0.3 to 1 kHz
(2) Current value of excitation current I: 0.1 to 1 A
(3) Length of excitation coil L: 70 mm
(4) Number of windings of excitation coil N: 200 turns
(5) Material quality of carburized tube: high Ni austenitic stainless steel
(6) Outer diameter of carburized tube: φ 15 to 25 mm
(7) Thickness of carburized tube: 0.9 to 1.25 mm
(8) Carburized depth of carburized tube: 27 to 46 μm As shown in FIG. 5, if $4 \leq K \leq 8$ is satisfied, the X signal becomes a negative value, and thus it is possible to sense variation in magnetic property, which is caused by the carburized portion on the inner surface of the carburized tube P0.

If $4 > K$ is satisfied, because the current value of the excitation current becomes smaller, or the excitation frequency becomes greater and the penetration depth becomes smaller, the magnetic field strength on the inner surface of the carburized tube P0 becomes smaller. Consequently, the magnetic permeability of the carburized tube P0 becomes smaller, and variation in magnetic property due to the carburization cannot be accurately sensed. On the other hand, if $8 < K$ is satisfied, because the frequency of the excitation current is a low frequency, so that the penetration depth becomes greater, but the voltage induced in the detection coil 12 becomes smaller, so that the sensitivity of the signal processing section 2 (gain of the amplifier 22) becomes greater. Hence, influence of the variation in conductivity becomes greater compared to the variation in magnetic property. As a result, it may be considered that the X signal becomes a positive value.

Accordingly, it can be said that it is possible to sense whether the carburization occurs or not on the inner surface of the steel tube P by inspecting the steel tube P that is the inspection target after the conditions of the excitation coil 11 are so set as to satisfy $4 \leq K \leq 8$, and the threshold value stored in the determination section 27 is set to be zero, for example.

Figure 6A:
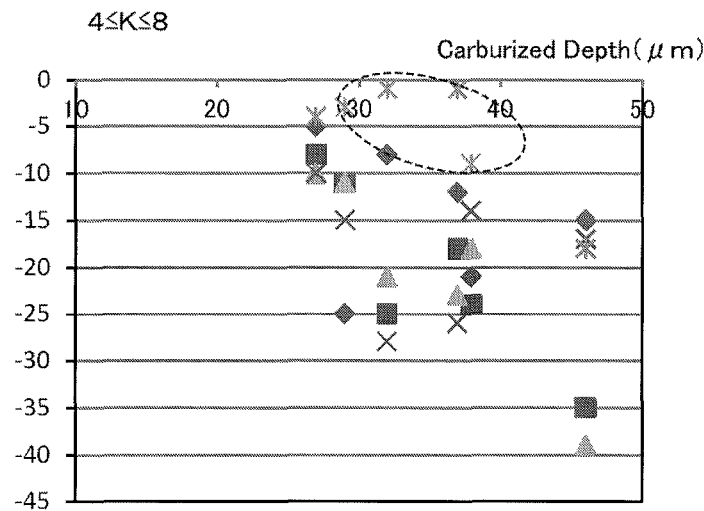
FIG. 6A is a diagram showing data satisfying 4≤K≤8, which are extracted from data shown in FIG. 5, and results from investigation on a relation between detection signals and carburized depth.
Figure 6B:
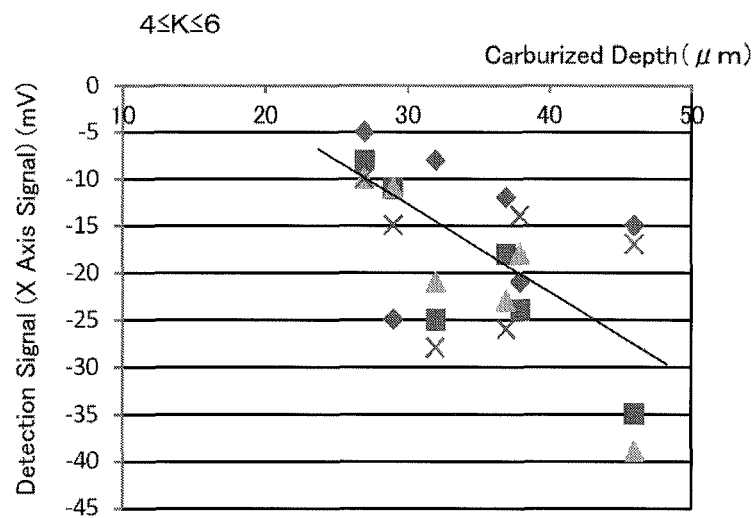
FIG. 6B is a diagram plotting data shown in FIG. 6A excluding data of K=8 (4≤K≤6 after the exclusion).

FIG. 6A is a diagram showing data satisfying $4 \leq K \leq 8$, which are extracted from data shown in FIG. 5, and results from investigation on a relation between detection signals and carburized depth. FIG. 6B is a diagram plotting data shown in FIG. 6A excluding data of K=8 ($4 \leq K \leq 6$ after the exclusion). In FIG. 6A and FIG. 6B, data plotted with the identical symbol indicates data having the identical K.

As shown in FIG. 6A, there is a relatively preferable correlation between the detection signals and the carburized depth. Accordingly, it is possible to estimate the carburized depth to some extent based on the magnitude of the detection signal. It is, however, preferable to satisfy $4 \leq K \leq 6$, as shown in FIG. 6B, because the absolute value of the detection signal may become small in some cases in the case of K=8 (data surrounded by a dotted line in FIG. 6A).

REFERENCE SIGNS LIST

1 Detection sensor
2 Signal processing section
11 Excitation coil
12 Detection coil
21 Oscillator
22 Amplifier
23 Synchronous wave detector
24 Phase rotator
26 A/D converter
27 determination section
100 eddy current testing apparatus
P Steel tube
P0 Carburized tube

The invention claimed is:
1. A method for sensing whether carburization occurs or not on an inner surface of a pipe or tube by an electromagnetic testing, comprising:
a first step of inserting a carburized pipe or tube in which occurrence of carburization on an inner surface thereof is known into an excitation coil and into a detection coil, and determining a value of a parameter K represented by the following Equation (1):

$$K=(I \cdot N/L) \cdot F^{-3/2} \qquad (1)$$

so as to sense the carburization that has occurred in the carburized pipe or tube based on an output signal outputted from the detection coil, where a current value of an excitation current passing through the excitation coil is defined as I(A), a length of the excitation coil is defined as L (mm), a number of windings of the excitation coil is defined as N, and a frequency of the excitation current passing through the excitation coil is defined as F (kHz); and a second step of setting conditions of the excitation coil so as to obtain the value of the parameter K determined in the first step, and thereafter, inserting a pipe or tube that is an inspection target into the excitation coil and into the detection coil and sensing whether carburization occurs or not on an inner surface of the pipe or tube based on an output signal outputted from the detection coil.

2. The method of sensing whether carburization occurs or not on an inner surface of a pipe or tube according to claim 1, wherein in the second step, the conditions of the excitation coil are set such that the value of the parameter K satisfies $4 \leq K \leq 8$.

* * * * *